United States Patent
Hardman et al.

(10) Patent No.: US 7,037,470 B2
(45) Date of Patent: *May 2, 2006

(54) SYSTEM AND METHOD FOR BIOCHEMICAL ASSAY

(76) Inventors: Clayton M. Hardman, 8284 Country Lake Dr., Orangevale, CA (US) 95662; Jaspal Mahal, 289 Anita Way, Yuba City, CA (US) 95993; Sanjay R. Mishra, 2923 Florence, #202, Berkeley, CA (US) 94705; Kuldip Sra, 104 Woodview Cir., San Ramon, CA (US) 94583

( * ) Notice: Subject to any disclaimer, the term of this patent is extended or adjusted under 35 U.S.C. 154(b) by 102 days.

This patent is subject to a terminal disclaimer.

(21) Appl. No.: 10/618,923

(22) Filed: Jul. 14, 2003

(65) Prior Publication Data

US 2004/0052686 A1    Mar. 18, 2004

Related U.S. Application Data

(62) Division of application No. 09/186,793, filed on Nov. 5, 1998, now Pat. No. 6,592,820.

(51) Int. Cl.
  *G01N 27/00*    (2006.01)

(52) U.S. Cl. .............. 422/65; 422/63; 422/67; 422/100; 436/43; 436/47; 436/54

(58) Field of Classification Search .............. 422/63, 422/65, 67, 100, 101, 104; 436/43, 47–49, 436/54, 174, 175, 180, 514, 526, 528; 209/213, 209/215; 210/222, 233
See application file for complete search history.

(56) References Cited

U.S. PATENT DOCUMENTS

| | | | | | |
|---|---|---|---|---|---|
| 4,219,335 | A | * | 8/1980 | Ebersole | 436/518 |
| 4,413,296 | A | * | 11/1983 | Jeffers | 360/315 |
| 5,654,854 | A | * | 8/1997 | Mallary | 360/327.3 |
| 5,773,307 | A | * | 6/1998 | Colin et al. | 436/526 |
| 5,925,573 | A | * | 7/1999 | Colin et al. | 436/525 |
| 5,981,297 | A | * | 11/1999 | Baselt | 436/514 |

* cited by examiner

*Primary Examiner*—Jeffrey R. Snay
(74) *Attorney, Agent, or Firm*—Philip M. Weiss; Weiss & Weiss

(57) ABSTRACT

A system for making a biochemical assay of each of plurality of provided specimens, comprising: a plurality of receptacles, a sensor for providing a resistance, a mechanism and a controller.

12 Claims, 12 Drawing Sheets

| Configuration | Bridge Bias | | Magnetic Bias | | |
|---|---|---|---|---|---|
| | $V_B$ On T2-T3 Bias | OSC On T2-T3 Bias | External | | Internal OSC On T4-T5 Coil |
| | | | Permanent Magnet | OSC On TA-TB Coil | |
| 1 | X | | | | |
| 2 | X | | | | |
| 3 | | X | X | | |
| 4 | | X | | X | |
| 5 | | X | | | X |

Figure 10

SYSTEM AND METHOD FOR BIOCHEMICAL ASSAY

This is a divisional of application Ser. No. 09/186,793, filed Nov. 5, 1998, now U.S. Pat. No. 6,592,820.

FIELD OF THE INVENTION

Embodiments of the present invention relate to the detection of biochemical substances using a giant magnetoresistive effect.

BACKGROUND OF THE INVENTION

The detection of minute quantities of biochemical substances in a specimen of animal body fluid is important, for example, in the early detection of disease. Conventional methods of specimen analysis that are feasible in a commercial setting include Enzyme Linked Immunosolvent Assay (ELISA), Western blot, Immunofluorescent, and Heme Agglutination (HA). These methods may be performed automatically by equipment including the "System 36 AutoBlot" marketed by Genelabs Diagnostics (Singapore) a subsidiary of Genelabs Technologies, Inc.; or the "Automated RIBA Processor" marketed by Chiron Corp. Other laboratory instrumentation may be used manually, including an ELISA plate reader, a fluorometer, and/or a luminometer. Conventional automatic equipment is bulky and expensive to acquire and maintain. And, manual equipment is labor intensive to use. Consequently, specimen analysis is costly. In some communities, a lack of specimen analysis has led to lengthy turn around delays. Such costs and delays interfere with the wide application of specimen analysis as a diagnostic practice. As a result, disease in animals including humans continues unchecked in its early stages.

A conventional biochemical assay performed in a laboratory may include the detection of microscopic paramagnetic particles (PMPs) bound to a giant magnetoresistive (GMR) sensor by specific intermolecular recognition bonds. PMPs are detected as a difference in the resistance of a GMR sensor having a bound PMP compared to a reference GMR sensor having no bound PMP. The difference may be detected using sinusoidal magnetic bias for the GMR sensors and a conventional lock-in amplifier technique. Accuracy of the assay depends in part on the removal of PMPs not bound according to the specific intermolecular recognition bond of interest.

The biochemical assay described above is prohibitively expensive for commercial application outside a laboratory setting. Part of this cost is in labor intensive steps including manual preparation of the specimen in combination with PMPs and manual removal of PMPs to improve assay accuracy. Another part of the cost becomes prohibitive as the number specimens to be tested in a given period of time is increased to a commercially practical level. Without method steps that prevent exposure of common surfaces to more than one specimen, an unsatisfactory risk of false positive assays may result.

In light of the demand for high volume biochemical assay services in combination with the lack of satisfactory techniques for maintaining low cost per specimen and low probability of false positive results, the need remains for improved systems and methods for biochemical assay.

SUMMARY OF THE INVENTION

A system for making a biochemical assay of each of a plurality of provided specimens, according to various aspects of the present invention, includes a plurality of receptacles, a sensor for providing a resistance, a mechanism, and a controller. Each receptacle contains a specimen and includes a surface for binding a paramagnetic particle (PMP) to the surface. When biased by a magnetic field, the presence of a PMP affects the resistance of the sensor in accordance with a giant magnetoresistive effect. The mechanism positions each respective surface in working proximity to the sensor for providing a respective resistance. The controller controls the mechanism for recording indicia of each respective resistance.

By providing a receptacle for each specimen, apart from the sensor, each receptacle may be discarded and the sensor reused without risk of contact of the sensor with more than one specimen. Such isolation avoids contamination between specimens and consequently avoids false positive assay results.

Because no specimen comes in contact with the sensor, the device may quickly perform an assay on each of a large number of specimens. The cost and time involved in repeated sterilization of the sensor is avoided.

In a variation, a system for making a biochemical assay of a provided plurality of specimens, according to various aspects of the present invention, includes a receptacle for each specimen, a sensor for providing a resistance, and a detector. Each receptacle includes a surface for binding a paramagnetic particle to the surface. The sensor provides a resistance according to a giant magnetoresistive effect when the sensor is positioned in working proximity to each respective surface. And, the detector, being coupled to the sensor, provides a signal that conveys indicia of each respective resistance.

In a variation, a plurality of sensors is arranged in an array coupled to a differential amplifier. The array is addressed by a row ring counter and a column ring counter. Each addressed cell is coupled in turn in a bridge circuit to the differential amplifier. The differential amplifier provides a signal that conveys indicia of the resistance of each sensor according to a sequence.

By forming the array, ring counters, and differential amplifier as an integrated circuit, coupling the plurality of sensors to the detector is simplified. In operation, an assay of a specimen in working proximity to the plurality of sensors provides greater resolution for determining a concentration of PMPs in the specimen.

A receptacle in accordance with various aspects of the present invention includes an array of wells, each well having an interior surface opposite a surface against which a sensor may be located. By locating a sensor against such a surface, the distance between the sensor and the interior surface is accurately determined, improving assay accuracy results.

In a variation, the receptacle includes an array of wells within a specimen containment wall. Agglomeration of PMPs within a well is avoided. Improved assay accuracy results.

BRIEF DESCRIPTION OF THE DRAWING

The preferred exemplary embodiment of the present invention will be described with reference to the drawing, wherein like designations denote like elements, and:

FIG. 10 is a table of bridge bias and magnetic bias configurations;

DETAILED DESCRIPTION OF THE PREFERRED EMBODIMENT

Figure 1:
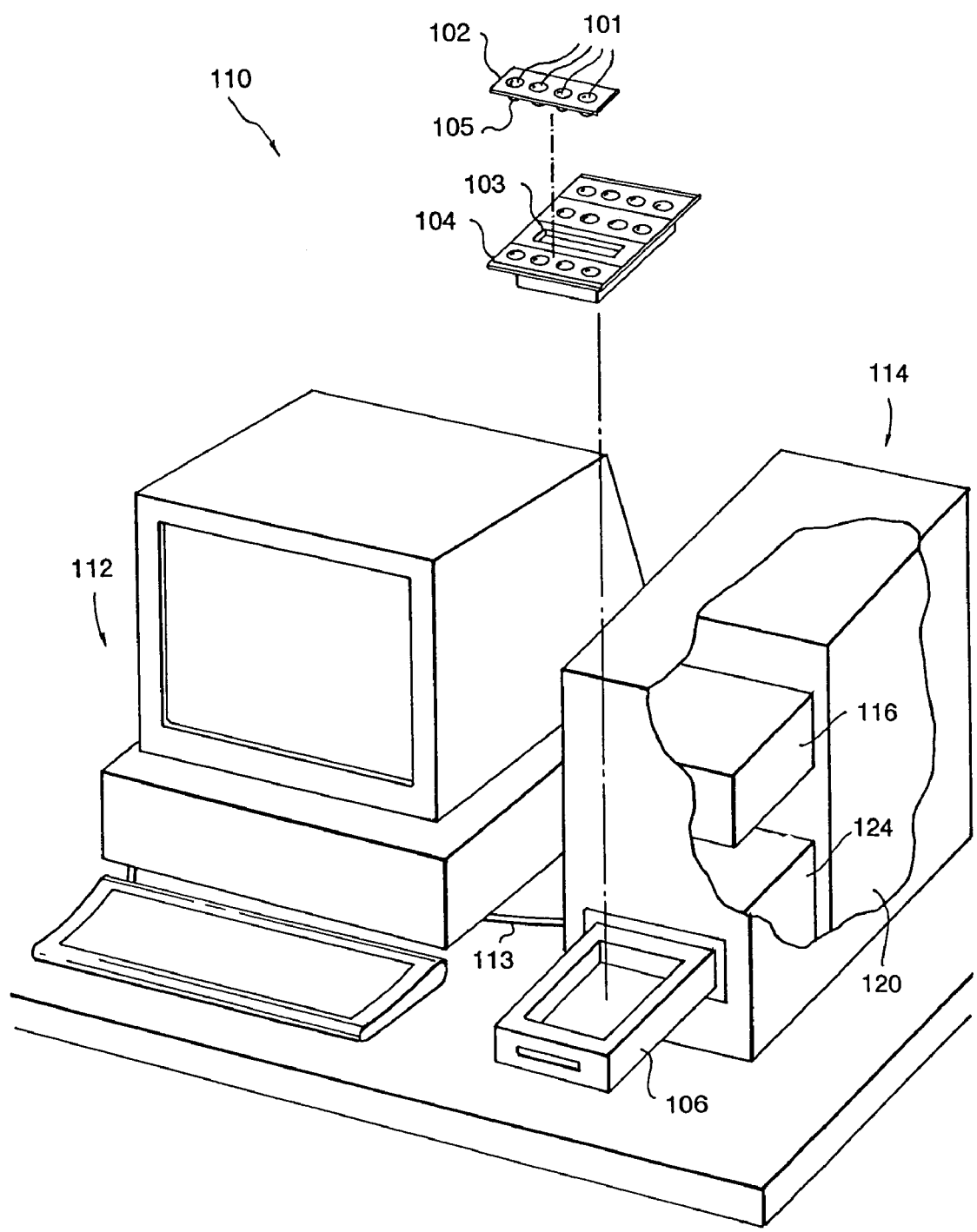
FIG. 1 is a perspective view of a system in one embodiment of the present invention.

Systems and methods of the present invention accomplish a biochemical assay of a fluid specimen. A biochemical assay includes any examination of a specimen for the determination of a characteristic of a biochemical substance. For instance, such an assay may be used to determine the concentration of a substance in the specimen or a property of a substance. Such a substance may be a protein, an enzyme, a portion of a DNA molecule, a carbohydrate molecule, a drug (medicinal or harmful), a hormone, a marker (e.g., cancer marker, cardiac marker, a pathogenic disease marker, etc.), a blood cell, a bacterial cell, a fungal cell, a virus, or a parasite, to name a few representative examples. Properties of substances which may be determined by a biochemical assay may describe cell adhesion binding, ligand-receptor binding, antibody-antigen binding, binding affinity or unbinding force (e.g., molecular or intercellular), hybridization events, or the composition of a molecule (e.g., DNA or peptide). The liquid specimen may be prepared from solid form by forming a solution or suspension, or may be prepared from a liquid by dilution, concentration, or mixing with chemical or biochemical agents or reagents. Such a specimen may include various plant or animal body fluids including blood, plasma, serum, urine, spinal fluid, lymph, digestive fluid, or a secretion of a gland such as saliva, semen, etc. and may include soil pollutants, water pollutants, or air pollutants.

A biochemical assay of the present invention includes any assay that includes detection of one or more paramagnetic particles (PMPs) that have adhered to a surface. For example, such an assay may in general include the steps of: (a) preparing a surface with a first substance; (b) preparing PMPs with a second substance; (c) exposing, for a predetermined time period, a mixture of a specimen and the prepared PMPs to the prepared surface so that some PMPs attach to the surface according to a desired binding; (d) moving PMPs away from the surface that have not participated in the desired binding; and (e) detecting the presence of one or more PMPs that remain near the surface by a magnetic and electronic measurement technique.

The results of an assay are generally useful for storing (e.g., for off-site analysis or trend analysis), analyzing (e.g. peak determination or summarizing), alerting an operator, or controlling equipment. Indicia of measurement results of a biochemical assay may be suitably conveyed by electronic signals including analog voltages or currents, or digital signals in parallel or serial format. Signal analysis may include quantization, comparison to threshold numeric limits in analog or digital form, comparison to related (or otherwise unrelated) specimens, and/or aggregation of multiple measurements over time or aggregation of measurements over several related (or otherwise unrelated) specimens. Comparisons may be used to verify proper system operation and to form an average for reducing variation in reported results. For example, the same receptacle and specimen may be sequentially placed in working relation with more than one sensor and the results compared or combined. Further, several readings of the specimen by the same sensor may be made and analyzed for trend, average, scatter, minimum, or maximum results.

A system for biochemical analysis, according to various aspects of the present invention, includes a console for operator controls, displays, and data processing, and a chemical analysis unit for performing a biochemical assay. For example, system 110 of FIG. 1 includes console 112 and analyzer 114 coupled by suitable signal cabling 113.

A console for use with a system of the present invention includes any console capable of controlling (or supervising) the operation of the chemical analysis unit and receiving a signal that conveys a result of a chemical analysis. For example, console 112 includes a conventional computer workstation having a processor, a memory, a data storage device (e.g., disk and or tape), a keyboard, a display, various peripherals (not shown) such as a network interface, a printer, an audio interface (e.g., for alarms), and various programs for controlling system operation such as an operating system, process and measurement subsystem control software, network communication software, and data processing programs. Console 112 also includes a conventional digital signal interface for communication with analyzer 114 over cable 113. Such communication includes process control command messages sent to analyzer 114 (e.g., initialize, start, stop, step, set parametric values or thresholds, etc.), process status messages received from analyzer 114 (e.g., analyzer ready, current state of parametric values or thresholds, current state of mechanical components, notice of awaiting action by operator, identification of the specimen or group of specimens. undergoing a process step, notice of an alert condition, current quantity of supplies, etc.), and process results (e.g., specimen pass/fail, specimen characteristic name and measured value, time of day, duration of test, etc.).

In a variation, multiple chemical analysis units are coupled via a conventional network to a common console. In a second variation, multiple consoles are coupled to one or more analysis units via a conventional network to provide information and/or control at multiple physical locations.

A chemical analysis unit according to various aspects of the present invention includes any unit capable of performing a biochemical assay of the type discussed above. For example, a chemical analysis unit herein called analyzer 114 accepts, tests, and returns specimens in quantity. For system 110, specimens are accepted from an operator and returned to an operator. In a variation, specimens are accepted from and returned to a conventional materials handling subsystem, for example, a robot or conveyor.

Specimens for use with a system of the present invention are each contained in a receptacle. A receptacle according to various aspects of the present invention includes any container for fluid handling having an interior surface in contact with the specimen. For example, for system 110, four cup-like receptacles 101 are joined by a strip about an upper portion of each respective receptacle to form specimen carrier 102 and 103.

Specimen tray 104 facilitates mechanical protection, identification, preparation, storage, handling, and disposal of multiple specimen carriers 102 and 103. The strip portion of each facilitates vertical insertion and removal from specimen tray 104 and facilitates location of the base 105 of each receptacle 101 a predetermined distance relative to specimen tray 104. Specimen carrier 102 and tray 104 may include mechanical or electronic features that identify each specimen, for example, orientation limitations and/or machine readable indicia of patient identifier, receptacle serial number, date, test sequence number, etc. Tray 104 provides convenient fluid access to the top of specimen carriers 102 and 103 and provides convenient electromagnetic access through the bottom of specimen carriers 102 and 103.

In a variation, multiple trays are installed in a cassette. Such a cassette further facilitates mechanical protection, identification, preparation, storage, handling, and disposal of a large number of receptacles and specimens. An analyzer capable of accepting such a cassette may have a mechanism for operating on one or more trays without removing each tray from the cassette. For example, a mechanism may have multiple fingers, each placed above and/or below one or more trays in a cassette. In a variation where all fluid access to a receptacle has already been completed, fingers provided under each receptacle may be sufficient for detection of PMPs.

In a variation, each tray is moved out of the cassette at least so far as is necessary to gain fluid and electromagnetic access to each specimen.

Where a minimum of operator manual intervention is desired, receptacles may be arranged in fixed relation in a one or two dimensional array or web. Conventional material handling equipment cooperates with a suitable mechanical interface in the analyzer to permit stepwise movement of the web, the detector, or both. Movement may be along the length of the web and/or across the width of the web.

For system 110, receptacles, specimen carriers, and specimen trays may be formed of materials for economic disposal after a single use.

Receptacles are preferably formed of a disposable, nonmagnetic material suitable for forming a bottom membrane with a thin, mechanically and thermally stable thickness. For example, receptacle 101 may be formed of one or more plastic materials including polyvinyl carbonate, polycarbonate, a membrane of the type marketed by Schleicher & Schuell, GmbH under the trademark NYTRAN, polyvinylidene difluoride (PVDF), and polystyrene. A receptacle formed of one material may be formed by any conventional process such as casting, extrusion, or machining. Multiple materials may be joined to form a receptacle by any conventional process such as gluing or sonic welding. Receptacle 101 may be formed entirely of polystyrene with a volume of about 1 milliliter, an interior diameter of about 7 millimeters, and a base 105 having a thickness 'b' in the range 0.5 millimeter to 1 millimeter. When the material used to form base 105 provides a fairly stiff membrane, tray 104 may be formed of a more flexible material to facilitate conforming the base 105 of a receptacle to the top surface 333 of a sensor.

Specimen tray 104 may be formed of a material that economically withstands repeated use and sterilization, for example, a plastic or metallic material. Tray 104, may be formed of conventional materials (e.g. alloys, impregnated plastics, or composite materials) to form a portion of an electrical and/or magnetic shield about a specimen.

Analyzer 114 is of conventional mechanical construction, except as described below, and primarily includes specimen transport 106, specimen dispenser/decanter 116, PMP detector 124, specimen/detector positioning system 120, and a conventional interface (not shown) for communication with console 112 via cable 113. Analyzer 114 also includes conventional facilities including power supplies, a supply of prepared PMPs, one or more fluid supplies, and one or more bins, tanks, or drains for waste materials.

Figure 2:
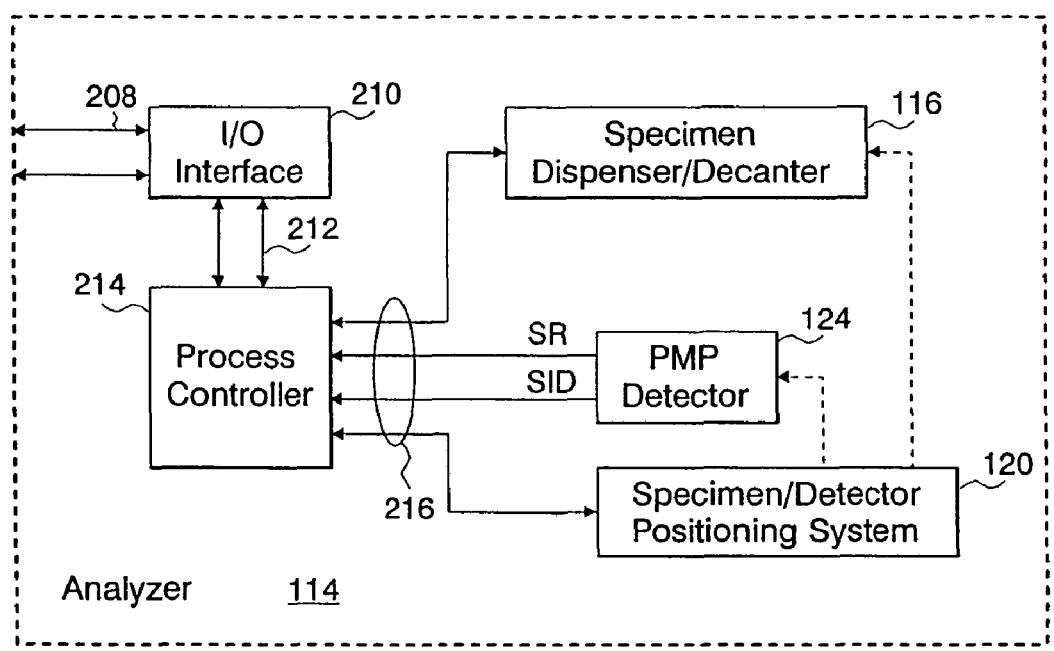
FIG. 2 is a functional block diagram of the analyzer of FIG. 1.

Analyzer 114 performs a biochemical assay of the type described above in a manner which may be better understood from the functional block diagram of FIG. 2. The functions of analyzer 114 are performed by process controller 214 in cooperation with input/output interface 210, specimen dispenser/decanter 116, PMP detector 124, and specimen/detector positioning system 120.

An I/O interface includes any input/output circuit for communicating messages between portions of a computer controlled system. For example, I/O interface 210 receives and sends signals on line 208 conveying messages as discussed above. Line 208 may include one or several electrical conductors. I/O interface 210 may include conventional circuits for point-to-point or network communication. I/O interface 210 communicates with process controller 214 via one or more conventional signals on line 212.

A process controller includes any circuit for performing a sequence of steps that safely performs a biochemical assay. For example, process controller 214 includes a conventional microcomputer system having memory devices (e.g., RAM, ROM, disk, etc.) and conventional machine control interfaces. Process controller 214 executes programmed instructions to perform a method, according to various aspects of the present invention, discussed below with reference to FIGS. 3 through 7. Process controller 214 receives status and data from, and commands operation of, other subsystem components via lines 216. Lines 216 may include one or more digital data buses and may include line 212 to I/O interface 210, as well as communication lines for memory devices as discussed above.

A specimen dispenser/decanter includes any electromechanical system for dispensing a fluid into a receptacle and decanting a fluid therefrom. For example, specimen dispenser/decanter 116 includes a multiple pipette dispensing and positioning system of the type marketed as the Multimec 96 System marketed by Beckman Coulter, Inc. Such a system includes reservoirs, a tip loading station, and a tip washing station and utilizes interchangeable pipette heads and/or disposable tip heads. The tip washing station includes tanks, fluid pumps, and vacuum pumps. Up to ninety-six pipettes are positioned in one motion over tray 104 for independent or simultaneous dispensing into specimen receptacles. The positioning functions of system 116 may be accomplished by conventional robotic control, for example, with the Multimec 96 System, a Core System with OCRA robot arm as marketed by Beckman Coulter, Inc. may be used.

Figure 3:
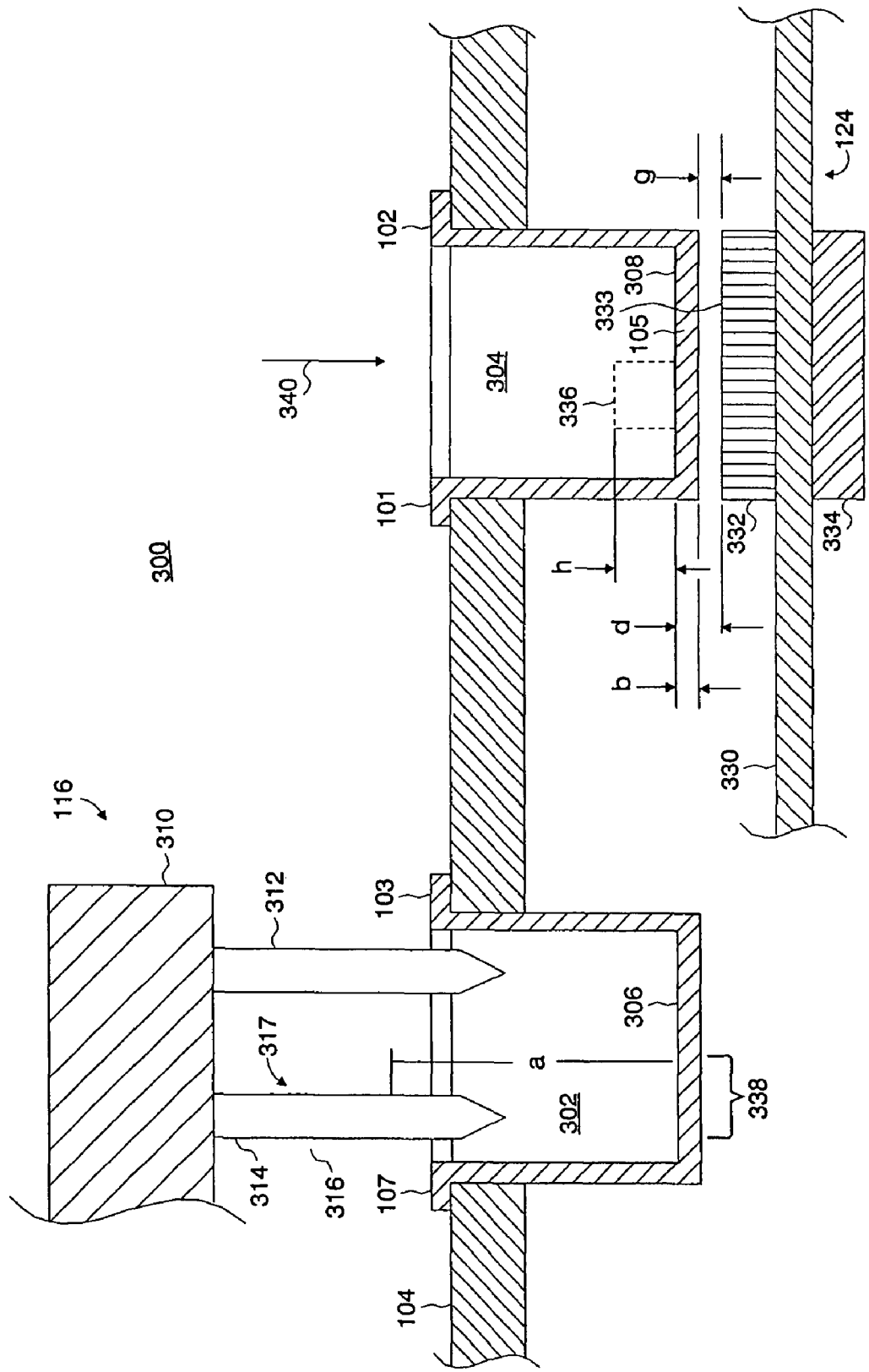
FIG. 3 is a cross section of a portion of the specimen dispenser/decanter and the PMP detector of FIG. 1.

The structure and operation of specimen dispenser/decanter 116 may be better understood from a cross section of an exemplary implementation 300 of analyzer 114, as in FIG. 3. In FIG. 3, arm 310 of specimen dispenser/decanter 116 provides pipettes 312 and 314 into receptacle 107 of specimen carrier 103. Pipette 314 includes coil 316 that establishes a magnetic field within pipette 314 for PMP removal. Receptacle 107 contains fluid specimen 302 in contact with its interior bottom surface 306.

In operation any fluid is disposed through pipette 312 and decanted through pipette 314. Simultaneous operation of pipettes 312 and 314 accomplishes mixing or turbulence in a controlled manner. In other words, a desired turbulence may be created accurately (e.g., for PMP removal) using a predetermined fluid flow rate and duration.

Decanting of fluid from a receptacle may be accomplished by any conventional technique internal or external to analyzer 114. When internal, for example, decanting may include removal of fluid by suction through either pipette 312 or 314. For decanting small amounts of fluid, decanting may include drying using a gas from pipette 312. Any conventional gas may be used, for example, dry air.

Pipette 314 includes magnetic trap 317 having a magnetic field primarily within pipette 314. By keeping magnetic flux from magnetic trap 317 away from surface 306, especially region 338, interference with PMP movement and binding is reduced. Region 338 corresponds to a sensitivity region 336 of a sensor placed under receptacle 103 as shown under receptacle 102. Sensitivity region 336, in an exemplary variation, has planar dimensions on surface 308 of about 1 millimeter by about 1 millimeter and extends into specimen 304 a distance 'h' of about 10 microns.

In a variation magnetic trap 317 is located so as to develop a magnetic field near surface 306, especially in region 338, to facilitate binding affinity tests, and removal of PMPs (whether free, nonspecifically bound, or variously specifically bound).

A PMP detector according to various aspects of the present invention includes any detector having multiple sensors for detecting one or more PMPs near a surface and may include a switching circuit for activating one or more sensors in sequence. A sensor in a preferred variation includes a semiconductor integrated circuit assembly with one or more metallic structures, each being sensitive to a giant magnetoresistive (GMR) effect. For example, PMP detector 124 may include four sensors each to be located directly under a specimen receptacle 101 to provide specimen result signal SR to process controller 214 for each specimen and each row of specimen tray 104. Each sensor may include one or more GMR elements in combination with integrated signal conditioning circuits. For example, PMP detector 124 includes a semiconductor of the type fabricated by Nonvolatile Electronics, Inc. and described, for example, in U.S. Pat. Nos. by Daughton and assigned to Nonvolatile Electronics, Inc., including U.S. Pat. Nos. 5,569,544; 5,595,830; 5,617,071; and 5,729,137, all of which are incorporated herein by this reference.

A specimen/detector positioning system according to various aspects of the present invention includes any mechanical apparatus that brings a receptacle and a sensor into working relation and maintains them in working relation while a detection step is being performed. For example, specimen/detector positioning system 120 includes electromechanical devices and control programs performed for example by process controller 214. The electromechanical devices may include conventional motors (e.g., linear and rotational) and position sensors. These devices may be arranged centrally or distributed within analyzer 114. Such devices cooperate as a system by virtue of the control programs.

In a variation having one sensor for each receptacle, the specimen/detector positioning system may primarily move in one movement all receptacles to be within the working distance of all sensors. This movement may be accomplished via conventional materials handling apparatus and may be supplemented by techniques including a vacuum or pressurized atmosphere above and/or below the receptacle for assuring a predetermined distance between a receptacle and a sensor.

In a variation having one sensor for each receptacle of a row portion of an array of receptacles, the specimen/detector positioning system may also move all receptacles an incremental distance so as to align the sensors over a next portion of the array. In other variations, movement of the sensors or movement of both the receptacles and the sensors accomplishes positioning and maintaining during the detection step.

It is preferred to position a receptacle in static relation with a sensor during the detection step. In a variation, a larger portion of the receptacle is exposed to a smaller sensitivity region of a sensor by movement of the receptacle, the sensor, or both during the detection step.

A specimen/detector positioning system may cooperate with other subsystems in a system of the present invention. For example, specimen/detector positioning system 120 cooperates with process controller 214, specimen dispenser/decanter 116, and PMP detector 124. Process controller 214 receives status from and provides commands to specimen/detector positioning system 120 via lines 216. In analyzer 114, specimen dispenser/decanter 116 and PMP detector 124 are stationary. Specimen/detector positioning system 120 indexes (i.e. moves) specimen tray 104 to locate four pipettes of specimen dispenser/decanter 116 over, and four sensors of PMP detector 124 sequentially under, each row of specimen receptacles in specimen tray 104. Dashed lines between specimen dispenser/decanter 116, PMP detector 124, and specimen/detector positioning system 120 in FIG. 2 describe such mechanical cooperation which may include for example physical alignment stops, limit switches, and dedicated signal lines.

In a variation, the specimen tray (or cassette) is stationary, the specimen dispenser/decanter operates on all specimens simultaneously, and the PMP detector includes a sensor for each receptacle so that operation on all specimens is accomplished without movement occurring during sequential or simultaneous detection steps. The specimen/detector positioning system in such a variation accomplishes, among other objectives, fine positioning and position maintaining steps by applying and removing, for example, a pressurized atmosphere to physically press each sensor and receptacle together.

In another variation, a specimen/detector positioning system moves all or a portion of a cassette of specimen trays.

In yet another variation, a specimen/detector positioning system additionally indexes the PMP detector sequentially from one group of receptacles to another.

The extent of a working relationship between a PMP detector and a receptacle according to aspects of the present invention may be better understood from a cross section of an exemplary implementation 300 of analyzer 114, as in FIG. 3. Specimen carrier 102 is located in specimen tray 104. Specimen tray 104 is held in position against a circuit board 330 of PMP detector 124 by a pressurized atmospheric force schematically represented by arrow 340. Specimen carrier 102 includes receptacle 101 that contains fluid specimen 304 in contact with its interior bottom surface 308. Sensor 332 is fixed to the top surface of circuit board 330, while magnet 334 is fixed to the bottom surface of circuit board 330. Circuit board 330 is held immobile with respect to the vertical movement of specimen tray 104, specimen carrier 102, and receptacle 101. Force 340 operates against specimen 304 and receptacle 101 to locate surface 308 a predetermined distance 'd' from the top surface of sensor 332.

A sensor, according to various aspects of the present invention, exhibits a region of sensitivity to the presence of PMPs defined herein as the distance at which the probability of detection of a single PMP is 50%. For example, sensor 332 is sensitive to the presence of one or more PMPs that may exist within sensitivity region 336. Sensitivity region 336 extends from sensor 332 across a gap (if any) between sensor 332 and receptacle 101, through the bottom of receptacle 101 and above surface 308. In one implementation, the distance between the interior surface 308 and the top of a sensor (illustrated as the distance 'g') in region 336 is established and maintained during detection in the range 0 to about 50 microns. The sensor is designed and operated to exhibit a height 'h' of region 336 above surface 308 during detection in the range 2 microns to 20 microns and preferably about 10 microns.

Table 1 describes several exemplary assays. In the table, the term antibody refers generally to a monoclonal or polyclonal antibody (e.g., containing IgG, IGM, or both). In the case of a viral antibody, such an antibody may be raised against a whole virus (e.g., live, attenuated, or viral lysate), against one or more recombinant proteins from one or more different parts of the viral genome, or against one or more synthetic peptides based upon an antigenic region of a sequence of the viral genome.

TABLE 1

| Type of Assay | Receptacle Coating | PMP Coating | Resulting Complexes |
|---|---|---|---|
| 1. Antigen Capture | antibody | second antibody | antibody + target antigen + second antibody + PMP |
| 2. Antibody Capture | antigen | conjugate of secondary antibody | antigen + target antibody + conjugate of secondary antibody + PMP |
| 3. Antigen Capture Inhibition | antibody | conjugate of target antigen | a. antibody + conjugate target antigen + PMP; or b. target antigen |
| 4. Antibody Capture Inhibition | antigen | conjugate of target antibody | a. antigen + conjugate target antibody + PMP; or b. target antibody |
| 5. DNA Hybridization | DNA probe | complementary DNA probe | DNA probe + target DNA + complementary DNA probe + PMP |
| 6. Cellular Hormonal or Steroid Inhibition | antibody | conjugate of target hormone or steroid | a. antibody + conjugate of target hormone or steroid + PMP; or b. target hormone or steroid |
| 7. Cellular Release Cytokine Capture | antibody | conjugate of second antibody | antibody + target cytokines + conjugate of second antibody + PMP |
| 8. Drugs of Abuse Capture Inhibition | antibody | conjugate of target drug of abuse | a. antibody + conjugate of target drug of abuse + PMP; or b. antibody + target drug of abuse |
| 9. Cellular adhesion Factor Inhibition | cells | conjugate of target antibody | a. cells + conjugate of target antibody + PMP; or b. cells + target antibody |

TABLE 1-continued

| Type of Assay | Receptacle Coating | PMP Coating | Resulting Complexes |
|---|---|---|---|
| 10. Dissimilar Multifactor Capture (type A) | On separate regions: 1. antibody-A; and 2. antigen-B | On separate PMPs: 1. second antibody-B; and 2. secondary antibody-C | 1. antibody-A + target antigen + second antibody-B + PMP; and 2. antigen-B + target antibody + secondary antibody-C + PMP |
| 11. Lipopolysaccharide Capture | antibody | conjugate of second antibody | antibody + target lipopolysaccharide + conjugate of second antibody + PMP |
| 12. Cell Surface Carbohydrate Marker Capture | antibody | conjugate of second antibody | antibody + target lectin + conjugate of second antibody + PMP |
| 13. Allergen Capture | antibody | conjugate of second antibody | antibody + target allergen + conjugate of second antibody + PMP |
| 14. Dissimilar Multifactor Capture (type B) | On separate regions: 1. antigen-A; and 2. DNA probe | On separate PMPs: 1. conjugate of secondary antibody; and 2. complementary DNA probe | 1. antigen-A + target antibody + conjugate of secondary antibody + PMP; and 2. DNA probe + target DNA + complementary DNA probe + PMP |

Figure 4:
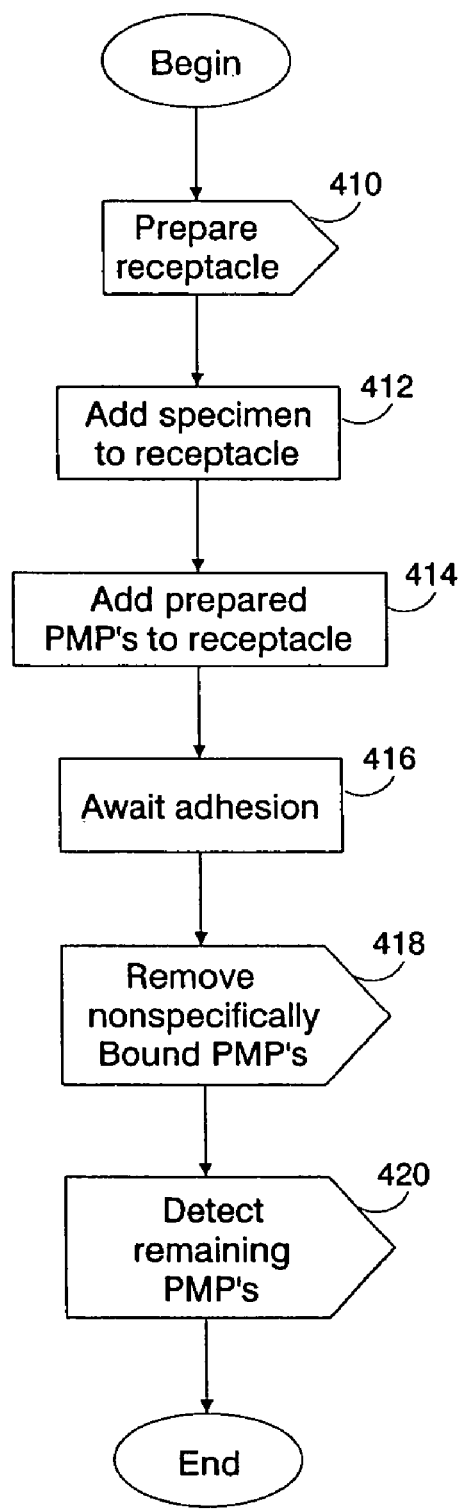
FIGS. 4–7 present a flow diagram of the operation of the analyzer of FIG. 2.

A system of the present invention includes any system for performing a biochemical assay that operates according to a method that includes binding PMPs to a surface, selectively moving PMPs away from the surface, positioning the surface and a detector in working relation, and detecting PMPs in the vicinity of the surface. For example, method 400 of FIG. 4 is performed by system 110 for a biochemical assay on specimens 302 and 304 as discussed above.

At step 410, a receptacle 101 is prepared for a particular assay. Preparation may be accomplished in a similar manner for any or all receptacles in specimen carrier 102, a tray 104, a cassette, or a web. On the other hand, preparation of receptacles may vary so that different assays are performed in different receptacles of a specimen carrier 102, a tray 104, a cassette, or a web. Step 410 may be performed external to analyzer 114 (as described below) or by analyzer 114, primarily using specimen dispenser/decanter 116, especially pipettes 312 and 314, discussed above.

Figure 5:
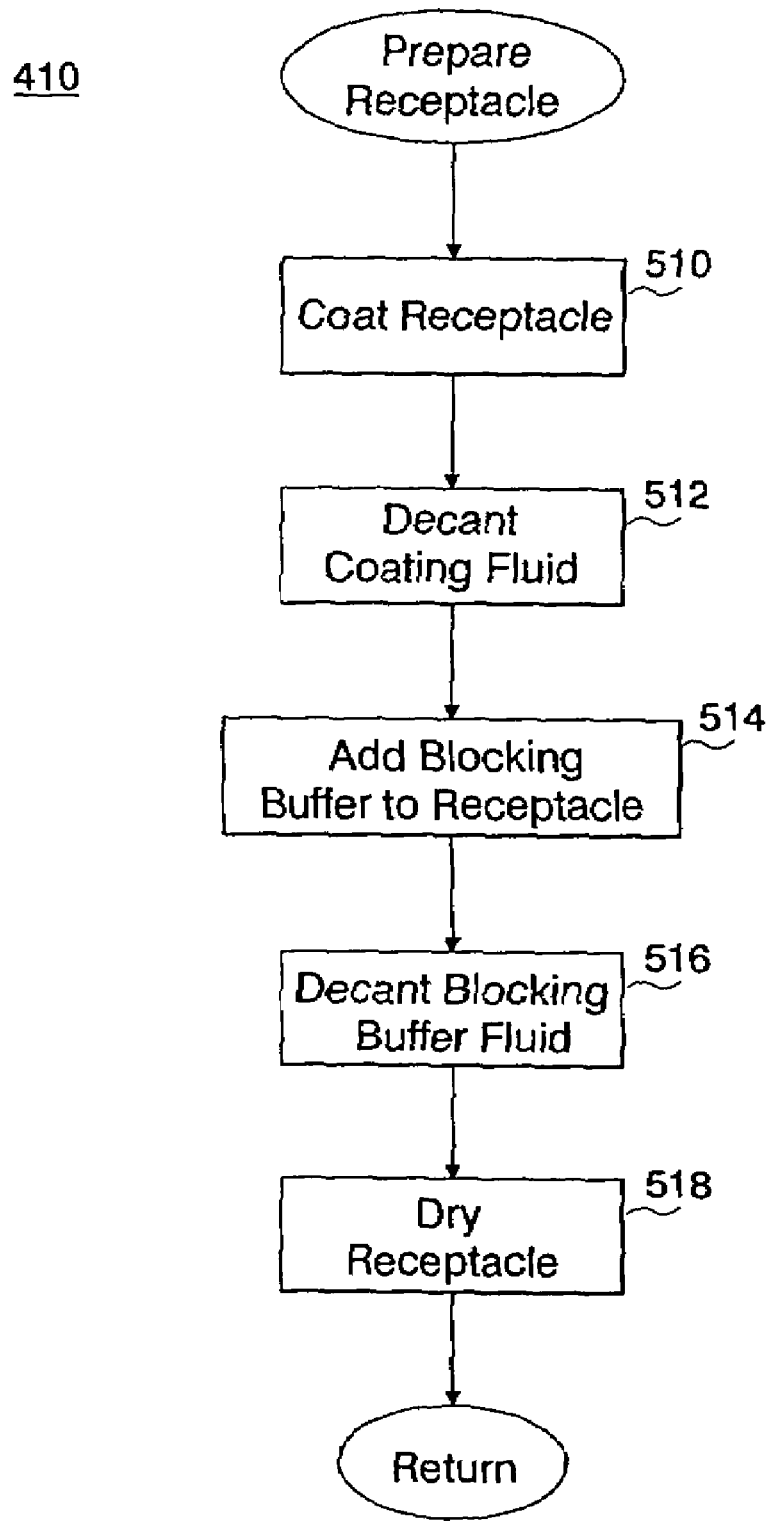
Figure 6:
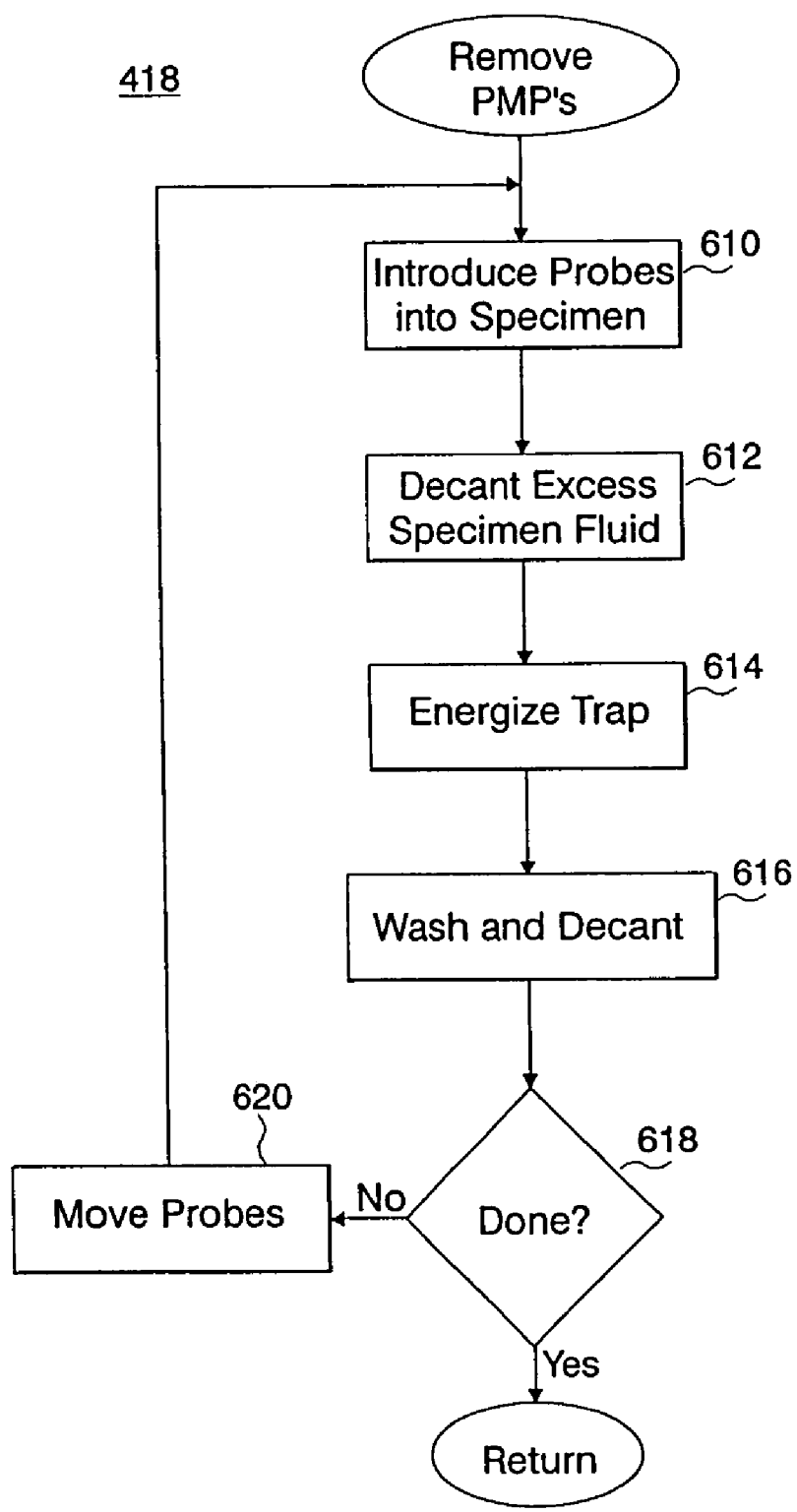
Figure 7:
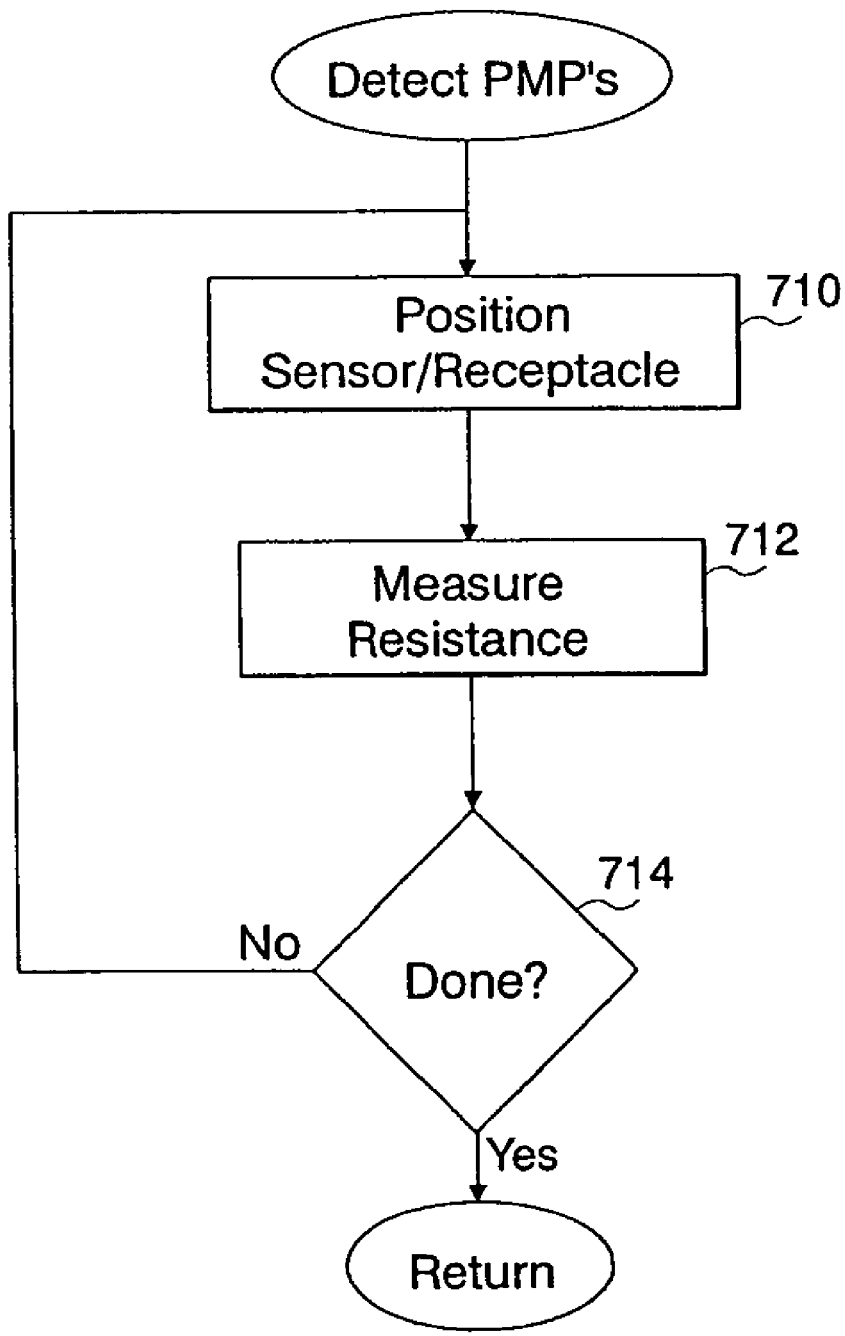

Preparation of the surface of a receptacle includes any method that activates the surface for specifically binding PMPs, for example, method 410 of FIG. 5. Coatings may bind to the receptacle surface by passive absorption or by covalent binding.

At step 510, surface 308 of receptacle 101 is coated by spraying surface 308 with a fluid reagent or by filling receptacle 101 with a fluid reagent. The fluid reagent may have a pH between 4.5 and 11 and is allowed to stand at ambient temperature and pressure for 0.5 to 24 hours to develop a coating, for example as described in Table 1.

At step 512, excess fluid reagent is then decanted. The extent of coating may be determined by comparing the amount of decanted fluid to the amount of fluid dispensed at step 510.

At step 514, a second fluid reagent is applied. The second fluid reagent includes a blocking buffer (e.g. bovine serum albumin, casein, or another conventional blocking buffer). The second fluid reagent is allowed to stand at ambient temperature and pressure for about 10 minutes to about 2 hours to develop a second coating. The second coating "fills" sites within sensitivity region 336 that were not filled by the first coating. The second coating prevents undesired materials from binding to surface 308 in sensitivity region 336.

At step 516, excess blocking buffer fluid is then decanted.

At step 518, prepared receptacles are dried and may be stored with a desiccant. Drying may be accomplished by dispensing a gas, for example warm, dry air, from pipette 312. In variations, prepared receptacles are freeze-dried and/or vacuum sealed for storage. For system 110, prepared specimen carriers 102 and 103 may be loaded into a specimen tray 104 or cassette for storage as an assembly.

The efficient coating of a receptacle for a particular assay may be determined by empirical analysis. For example, a series of experimental quantity and duration protocols may be prepared and analyzed for the extent of coating, for minimizing the cost of materials and energy expended, and for reducing the duration of the coating process. Conventional analysis techniques may be used including developing so-called calibration curves using incremental amounts of each experimental variable such as time, temperature, coating substances, washing substances, number of wash cycles, and the extent (if any) of low level vibration or rocking during coating, decanting, washing, and drying.

As an example, preparing a receptacle for detection of HIV in a blood sample includes the steps of adding to a clean receptacle 200 microliters of solution containing 20 micrograms of a mixture of proteins including for example gp-120, gp-41, and/or p-24 proteins. About 50% to 80% of the proteins will bind when the receptacle is held static at ambient temperature and pressure in a period of about 4 hours. About 40% to 50% of the sites available on the receptacle surface in the sensitivity region will be coated. By extending the period to about 12 hours, about 90% of the available sites may be coated. After decanting as described above, about 400 microliters of BSA is dispensed into the receptacle, allowed to fill available sites, and then removed by decanting.

At step 412, of FIG. 4, a fluid specimen is added to a prepared receptacle in any conventional manner. Contact of the specimen and coated surfaces of the receptacle may improved by any conventional mixing operation including, for example, rocking or low level vibration. For example, in system 110, an operator (or robotic materials handler) working under ambient conditions places in transport 106 a specimen tray 104 that holds specimen carriers having previously prepared receptacles. Specimen dispenser/decanter 116 accesses specimen fluid containers (not shown) via conventional fluid handling techniques using, for example, washable or disposable pipette assemblies, and then moves a portion of the fluid from a specimen container to a receptacle. The step of moving specimen fluid may be accomplished by moving any number of fluid specimens simultaneously, for example by using one pipette for each specimen.

Depending on the biochemical assay being performed, the conditions and duration of exposure of the specimen to the prepared receptacle may vary. For example, for an assay of human blood for HIV, the blood is introduced into a coated receptacle at a temperature between 18 degrees Celsius and 25 degrees Celsius for a period of 0.5 to 24 hours.

After exposure of the specimen to the coated receptacle surface, the receptacle is washed and decanted with a conventional wash buffer, such as phosphate buffered saline solution containing a detergent of the type marketed by ICI Americas, Inc., a subsidiary of Imperial Chemical Industries, PLC, under the trademark TWEEN 20. Washing operations are important to obtain optimal accuracy of assay results. Empirical analysis, as described above, may be used to determine aspects of an optimal washing operation for a particular assay including, for example, temperature of wash fluid, constituents of one or more wash fluids used, and the duration and agitation (if any) of the wash fluid in the receptacle.

At step 414, prepared PMPs are added to each receptacle. A prepared PMP includes a conventional PMP and a coating. Table 1 lists exemplary PMP coatings for use with particular biochemical assays. A paramagnetic particle or superparamagnetic particle (generally PMP herein) is a generally spherical particle consisting of paramagnetic material, for example, maghemite crystallites dispersed in polystyrene. Such PMPs of various compositions, size distributions, and coatings are commercially available from several suppliers including, for example, Dynabeads marketed by Dynal, Inc., Estapor superparamagnetic microspheres marketed by Bangs Laboratories, BioMag particles (nonspherical) marketed by PerSeptive Biosystems, and Sera-Mag magnetic microparticles marketed by, Seradyn, Inc. DYNABEAD, ESTAPOR, BIOMAG and SERA-MAG are trademarks of the respective aforementioned companies. The diameter of PMPs for a particular assay and particular sensor may be selected from the range 0.1 to 5.0 microns; however, the distribution is preferably narrow, for example, less than plus or minus 50%.

Coating PMPs, according to an aspect of the present invention, may be accomplished by any method that includes the steps of applying a first coating that has an affinity for the PMP and applying a second coating that has an affinity for the first coating. For example, a first coating may include glutaryldehyde (GTD) and a second coating may include an antibody. Each coating may be applied by (a) agitating (e.g., rocking, vibrating, shaking, or stirring) PMPs in a fluid containing the desired coating; and (b) removing coated PMPs from the fluid. Removal of PMPs from a fluid may be accomplished by applying a magnetic field to aggregate the PMPs from the fluid and decanting the fluid. After removal, PMPs may be washed and removed from the wash fluid using a similar magnetic aggregation technique. Prepared PMPs may be stored in a fluid or dried and stored as a powder with a desiccant.

In system 110, specimen dispenser/decanter 116 dispenses PMPs in a fluid form into each receptacle. The fluid containing prepared PMPs is handled in the same manner that specimen fluid is handled as described above. For accurate biochemical assays, the amount of specimen, the amount of PMPs, and in some cases the time allowed for resultant complexes to form may be carefully metered. For example, dispensing of specimen is performed in system 110 to an accuracy of plus or minus 5 to 20 microliters.

In a variation, PMPs may be dispensed repeatedly from one or more dedicated pipettes that make no contact with a specimen so that a washing or disposal step is avoided.

In a variation PMPs are dispensed into receptacles by a system external to analyzer 114. A fluid specimen is then disposed into a receptacle already contained prepared PMPs.

In another variation two or more varieties of PMPs are added at step 414. Two different prepared PMPs may be used for simultaneously detecting related biochemicals (e.g., antigen and antibody; or antibody and DNA probe). Different prepared PMPs may differ in geometry, weight, magnetic properties, or coatings. Sequential measurement for two or more biochemical assay results may be facilitated with the graded removal of PMPs discussed below.

At step 416, a time passes to allow resultant complexes to form in the receptacle. Each such resultant complex (e.g., as in Table 1) is bound to an interior surface of a prepared receptacle by an affinity force, for example, in the range of 50 to 500 piconewtons. The time may be in seconds or hours depending on the type of assay, the desired resolution of the assay, and the expected constitution of the specimen, the prepared PMPs, and the prepared receptacle. Resultant complexes of interest are said to be specifically bound as opposed to other components and complexes that are described herein as material that is nonspecifically bound.

In variations, one or more of steps 412 through 416 are accomplished at one or more stations external to analyzer 114.

At step 418, nonspecifically bound PMPs are removed. A method for removing nonspecifically bound material according to various aspects of the present invention includes any method employing a pipette with a magnetic trap. For example, method 418 of FIG. 6 employs specimen dispenser/decanter 116 of FIG. 3 to remove PMPs. Such a method may be repeated a predetermined number of times to, for example, improve the effectiveness of each removal operation.

At step 610, pipettes 312 and 314 are introduced into a receptacle 107 that contains PMPs to be removed. Pipettes 312 and 314 include sterile portions that come in contact with the specimen.

At step 612, excess specimen fluid is decanted from receptacle 107 in any manner as discussed above.

At step 614, magnetic trap 317 is energized. A magnetic trap includes any apparatus for developing a magnetic field within a pipette. For example, coil 316 encircles the exterior of a portion of pipette 314 and is energized by a current provided by specimen dispenser/decanter 116. The number of turns, placement of the turns, and magnitude and spectrum of the energizing current provide a field strength within pipette 314 in the range of 1 milligauss to 50 milligauss. For example, for a pipette of about 5 millimeters in diameter, a coil of 100 turns located a distance 'a' in of about 1 centimeter from surface 306 is energized with about 23 milliamps to produce at surface 306 a force on a 2 micron diameter PMP of about 100 piconewtons. In a variation, a similar field strength is provided by a permanent magnet.

At step 616, a wash fluid is passed from pipette 312 through the specimen and then drawn from receptacle 107 through pipette 314 and magnetic trap 317. Material that is nonspecifically bound is removed from the receptacle along with free PMPs and PMPs in combination with material that is not of interest. Pipettes 312 and 314 cooperate to perform a wash operation. A particular wash operation may be determined for a particular assay by empirical analysis as described above. Contact between the wash fluid and the receptacle may be improved by any method of mixing including, for example, varying the fluid flow in pipettes 312 and/or 314.

By locating pipette 314 near (e.g., directly over) area 337, the field created by magnetic trap 317 may effect removal of nonspecifically bound PMPs in an area later to be within the sensitivity region (e.g. 336) of a GMR sensor. By modulating the distance between magnetic trap 317 and surface 306, graded removal of PMPs may be accomplished. For example, depending on the resulting complex of the desired assay, a field strength at surface 306 as low as about 50 piconewtons may be sufficient to remove PMPs that are nonspecifically bound to the surface without disturbing specifically bound PMPs.

By modulating the current in coil 316, the effectiveness of the removal step may be adjusted for the graded removal of PMPs and nonspecifically bound material. For example, when modulation provides removal in steps, a series of PMP detection steps may be interspersed between removal steps for determining an affinity between surface 306 and a particular resultant complex of interest. The composition of various resultant compositions may also be determined in a variation wherein a sequence of different wash fluids (and/or modulation of the flow rate of wash fluid) is interspersed with PMP detection steps.

At step 618, it is determined whether removal of PMPs should be performed with respect to another receptacle. If not, control passes back to step 420. If so, pipettes 312 and 314 are first prepared for introduction into another specimen (if different from the current specimen) by washing or replacing tip portions and second moved to the next receptacle. Control then passes to step 610, whereupon steps 610 through 618 are repeated for the next receptacle In a variation, receptacles may be dried after washing and decanting as in step 616. Drying may be accomplished as discussed above with reference to step 518. Dried receptacles may also be sealed and/or stored at conditions suitable for the desired assay. Alternatively, receptacles may be sealed and/or stored while containing a suitable solution for preservation of the resulting complexes (if any).

At step 420, PMPs remaining within the sensitivity region of the PMP detector are detected. PMP detection, according to various aspects of the present invention, includes any method wherein a receptacle and detector are temporarily brought into working relation. For example, method 420 of FIG. 7 describes a portion of the operation of PMP detector 124 and specimen/detector positioning system 120 of FIG. 3. A sample having about one femtomole of resulting complexes is sufficient for reliable detection according to various aspects of the present invention.

At step 710, a receptacle and sensor are brought into working relation as described above. PMP detection may be performed at ambient temperature.

Figure 9:
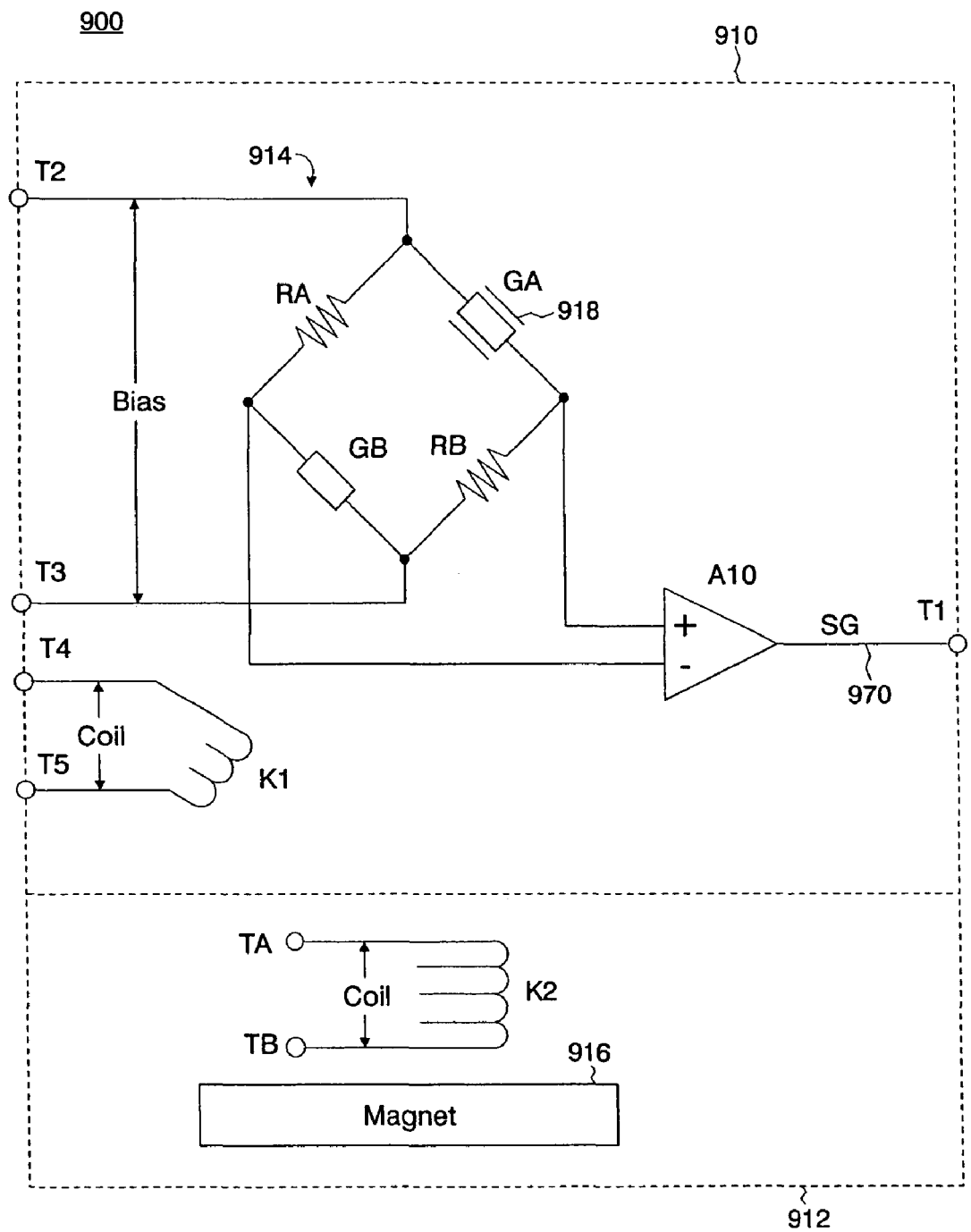
FIG. 9 is a schematic diagram of a sensor of the plurality of sensors 810 of FIG. 8.

At step 712, a resistance is measured of a portion of the sensor that responds to a giant magnetoresistive effect. A PMP within the sensitivity region of a GMR sensor affects the resistance of the GMR sensor as will be further discussed below with reference to FIGS. 9 and 10.

At step 714, it is determined whether detection of PMPs should be performed with respect to another receptacle. If not, methods 420 and 400 are complete. If so, PMP detector 124 is separated from the receptacle that has been tested in the immediately preceding operation of step 712; and, steps 710 through 714 are repeated with respect to the next receptacle.

Figure 8:
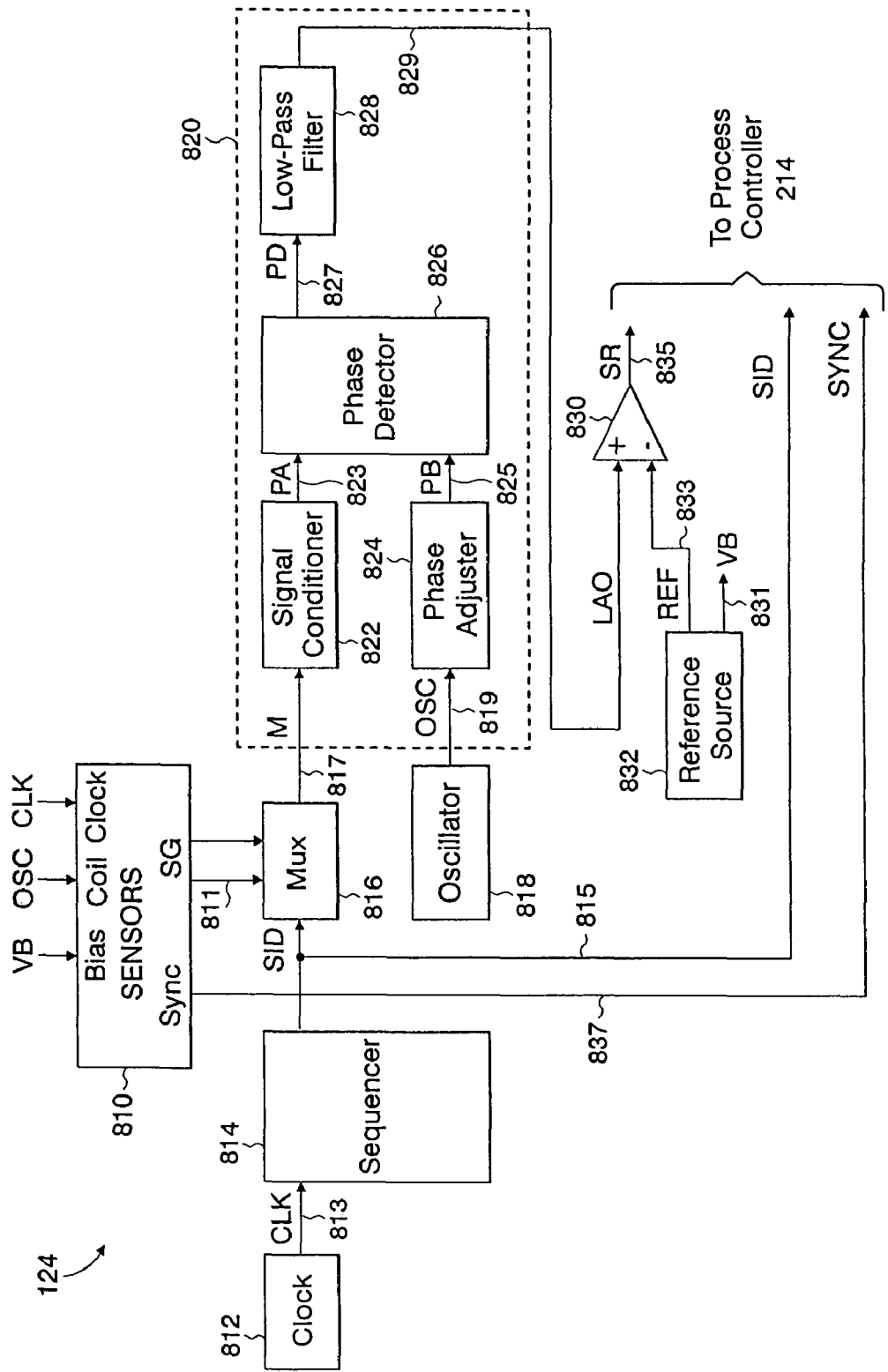
FIG. 8 is a functional block diagram of a portion of the PMP detector of FIG. 1.

A PMP detector, according to various aspects of the present invention, includes any detector that provides a specimen result signal with a specimen identifying signal. For example, PMP detector 124 provides signals SR on line 835 and SID on line 815 to process controller 214. An implementation of PMP detector 124, as described in pertinent part in the functional block diagram of FIG. 8, includes clock 812, sequencer 814, multiplexor 816, oscillator 818, lock-in amplifier 820, comparator 830, and reference source 832. PMP detector 124 is constructed of conventional analog and digital circuits, except as discussed below.

Clock 812 provides digital signal CLK on line 813 to sequencer 814. Signal CLK may have a frequency in the range of 0.05 Hz to 50 Hz and a conventional duty cycle for operating sequencer 814 at a period sufficient for completing a measurement from one sensor of the group of sensors 810. For example, when oscillator 818 provides signal OSC with a frequency of 300 Hz, ten cycles (i.e. about 33 milliseconds) may be needed for a stable signal SR to be provided by comparator 830 for one GMR sensor. When one GMR sensor is used per specimen, signal CLK in this example may have a frequency of about 30 Hz. When one GMR sensor is used with each specimen and increased accuracy of detection is desired, signal CLK may have a frequency of about 0.1 Hz corresponding to a period of about 100 seconds per specimen. In a variation where an array of 1024 GMR sensors is used for counting PMPs in one specimen, signal CLK may have a frequency of about 0.29 Hz for a period about 33 seconds (33 times 1024 milliseconds) per specimen.

Group of sensors 810 provides sensor conductivity signals SG on lines 811 to multiplexer 816. Group of sensors 810 includes four sensors, one to be located under each receptacle of specimen carrier 102 of FIG. 1. In a variation, group of sensors 810 includes any number of sensors including any number of arrays of sensors as discussed below with reference to FIG. 11.

Sequencer 814 provides digital signal SID on line 815 having a unique value for each sensor, therefore providing specimen identification. Line 815 also couples signal SID to multiplexer 816. In a variation, signal SID provides merely a synchronizing indication to identify the beginning of a sequence of sensor result signals SR. In such a variation, the identity of each sensor result may be determined by conventional time domain multiplexing techniques.

Multiplexer 816 responds to signal SID on line 815 by providing multiplexer output signal M on line 817 in accordance with one sensor conductivity signal SG received on line 811 and corresponding to a value of signal SID. Multiplexer 816 includes a conventional analog signal switching circuit for providing an output signal in accordance with a selected input analog signal without substantial loss of fidelity.

Oscillator 818 provides signal OSC on line 819 having a frequency in the range 100 Hz to 300 Hz and a waveform having a dominant fundamental frequency component, such as a sinusoid or square wave. The duration of PMP detection per GMR element is preferably less than 100 milliseconds when signal OSC is 200 Hz. At higher frequencies, shorter measurement duration may be used.

A lock-in amplifier according to various aspects of the present invention includes any circuit that accepts an analog signal and a reference signal and provides a direct current output signal in accordance with the amplitude of a component of the analog signal that corresponds in frequency to the frequency of the reference signal. For example, lock-in amplifier 820 is of the type described in "Frequency-domain Description of a Lock-In Amplifier" by Scofield, American Journal of Physics, vol. 62 part 2, pages 129–133 (February 1994), and "An Inexpensive Lock-In Amplifier" by Caplan, Review of Scientific Instruments, vol. 42, no. 5 pages 689–695 (May 1971) both incorporated herein by this reference. Lock-in amplifier 820 includes signal conditioner 822, phase adjuster 824, phase detector 826, and low-pass filter 828. Signal conditioner 822 includes AC amplification at the fundamental frequency of signal OSC to provide signal PA on line 823 in accordance with signal M on line 817. Phase adjuster 824 includes a conventional delay circuit set to assure the phase of phase adjuster output signal PB on line 825 matches the phase of signal PA. Phase adjuster 824 compensates for any phase difference that may result, among other causes, from spacial variations in magnetic bias field strength and from the AC signal characteristics of sensors 810, multiplexer 816, signal conditioner 822, and associated wiring.

Phase detector 826 includes a mixer or multiplier circuit for beating signals PA and PB to provide on line 817 signal PD having a DC component corresponding to the amplitude of signal M at the frequency of signal OSC.

Low-pass filter 828 attenuates components of signal PD above a minimum frequency, for example 1.0 Hz and may include DC gain to provide on line 829 lock-in amplifier output signal LAO.

Reference source 832 provides a DC reference voltage signal VB on line 831 for biasing group of sensors 810 and provides DC reference voltage signal REF on line 833. Signal REF has a DC voltage magnitude value that operates as a threshold for comparison. The threshold value is selected to differ (by a suitable margin) from the value of signal LAO when lock-in amplifier 820 is measuring a typical signal from sensor 332 having no PMP within the sensitivity region 336.

Comparator 830 includes a conventional analog comparator circuit. Comparator 830 provides a digital output sensor response signal SR on line 835 when the DC voltage magnitude of signal LAO on line 829 exceeds the DC voltage magnitude of signal REF on line 833. In effect, signal SR is asserted when the resistance of a selected sensor deviates from the expected resistance value by a substantial amount indicative of the presence of one or more PMPs within the sensitivity region of the selected sensor.

In a variation, the difference between lock-in amplifier output signal LAO on line 829 and reference signal REF on line 833 is measured with an analog to digital converter having several bits of resolution.

A sensor circuit of the present invention includes any circuit having a GMR sensor element. For example, group of sensors 810 includes one or more independent circuits, each circuit having a conventional GMR sensor element. Proper operation of such an element may require signals for bias, coil, and clock as may be better understood from the schematic diagram of sensor circuit 900 of FIG. 9. Sensor circuit 900 primarily includes an integrated circuit portion 910 and an external portion 912. Integrated circuit portion 910 includes wheatstone bridge circuit 914, planar coil K1, and amplifier A10. External portion 912 includes alternate coil K2 and alternate permanent magnet 916. In any particular.configuration, only one of coil K1, coil K2, and magnet 916 is required.

Coil K1 is preferably formed as a spiral under all GMR sensors formed on the integrated circuit substrate.

Bridge circuit 914 includes in a first leg resistor RA and GMR element GB; and, in a second leg, resistor RB and GMR element GA. Resistors RA and RB are of substantially equal resistance. GMR elements GA and GB exhibit substantially equal resistance in the absence of a PMP in the sensitivity region associated with GMR element GB. GMR element GA provides a reference resistance by being shielded generally from magnetic fields as indicated by shield 918. GMR elements GA and GB have a generally identical rectangular shape having a length in the range of from 10 to 500 microns. A GMR having an area of about 100 microns may be used to detect one PMP of about 1 to 2 microns in diameter. The surface area of the GMR exceeds the diameter of the PMP to increase the likelihood of successful binding.

Bridge circuit 914 receives a bridge bias voltage across terminals T2 and T3. A difference voltage across the bridge legs is amplified by amplifier A10 to provide signal SG on line 970 to terminal T1.

For proper operation, GMR elements GA and GB require a current passing through the respective element (as provided by bridge bias voltage) and element GB requires a bias magnetic field perpendicular to the face of the sensor element. Five configurations that provide these conditions are defined in FIG. 10 so as to provide signal SG with a frequency component at the frequency of signal OSC. When multiple sensors are bused to a common line for signal SG, sequential application of bridge bias and/or magnetic bias may be used for selectively activating each sensor.

A PMP detector having improved resolution according to various aspects of the present invention includes any integrated circuit having an array of GMR sensors coupled to a sequential selection circuit. A sequential selection circuit of the present invention includes any circuit that facilitates forming an output signal in accordance with a sequence of sensor output signals.

Figure 11:
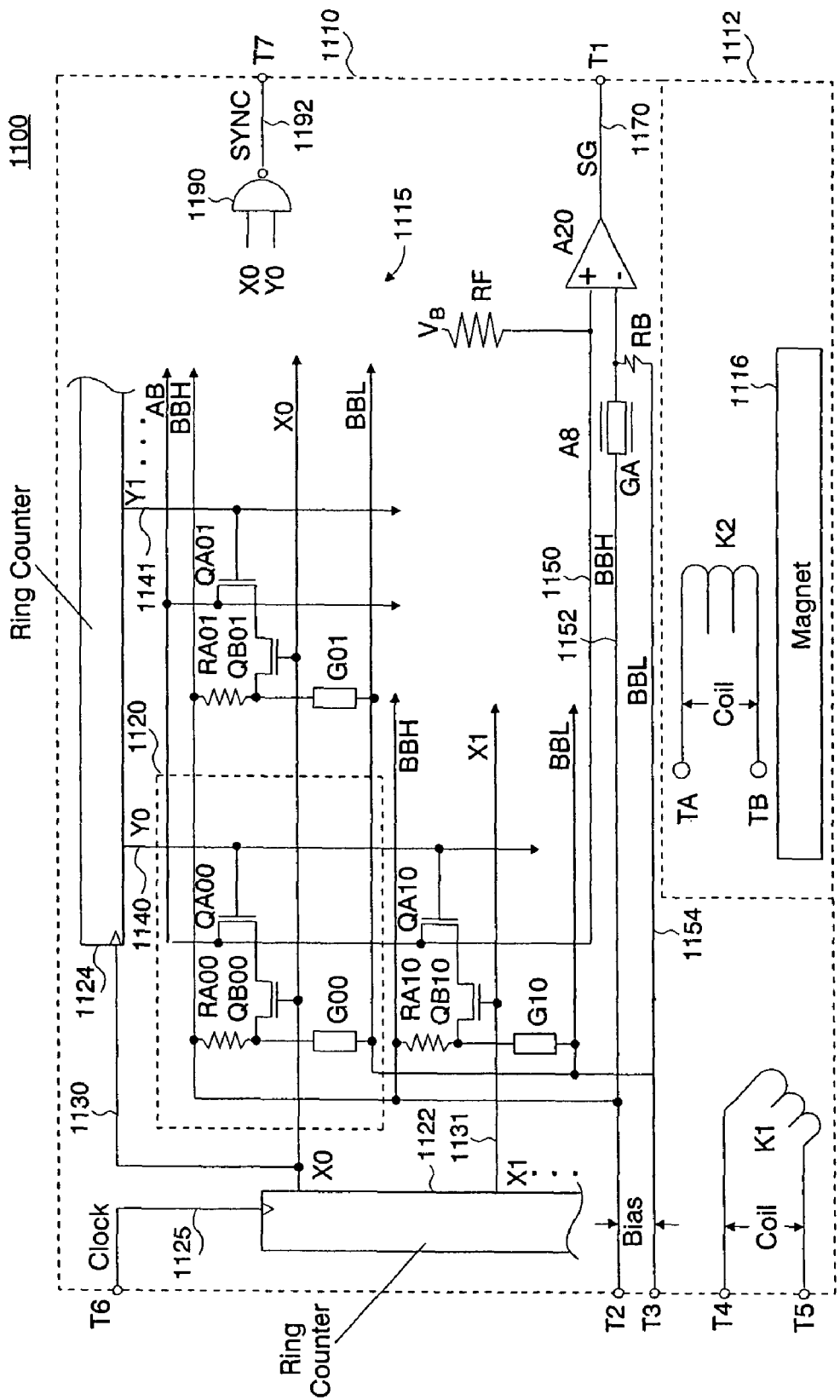
FIG. 11 is a schematic diagram of an array sensor for use in a variation of the plurality of sensors of FIG. 8.

For example, sensor 1100 of FIG. 11 includes integrated circuit portion 1110 and external portion 1112. Coil K1 of integrated circuit portion 1110 and coil K2 and permanent magnet 1116 of external portion 1112 have structure and function of the type described above with reference to FIGS. 9 and 10, except that magnetic bias provided by these elements uniformly biases all GMR elements in integrated circuit portion 1110.

Integrated circuit portion 1110 includes an array 1115 of sensor cells 1120 (R rows by C columns) coupled to an output bus 1150, a sequential selection circuit that includes terminal T6 for receiving a clock signal on line 1125, row ring counter 1122, column ring counter 1124, and analog amplifier A20.

In operation, all outputs $X_0$ through $X_R$ of row ring counter 1112 and $Y_0$ through $Y_C$ of column ring counter 1124 are not asserted, except one output of each ring counter which is asserted. For each active edge of a clock signal (e.g. signal CLK on line 813 or a multiple R*C thereof) received on line 1125 the asserted output of row ring counter 1122 advances one position from output $X_j$ to output $X_{j+1}$. When j=R. the asserted output advances to output $X_0$. For each active edge of signal $X_0$ coupled on line 1130 to column ring counter 1124, the asserted output of column ring counter 1124 advances from $Y_k$ to $Y_{k+1}$. When k=C, the asserted output advances to output $Y_0$. In other words, each cell of array 1115 in turn receives an asserted row signal concurrent with an asserted column signal. For example, in response to the assertion of row and column signals $X_0$ and $Y_0$, FETs QA00 and QB00 are turned on to couple resistor RA00 and GMR element G00 to line 1150. Resistor RF provides FET bias voltage derived from reference voltage signal VB.

A bridge bias voltage (between signals BBH and BBL) across terminals T2 and T3 provides signal AB from cell 1120 onto line 1150. This bridge bias voltage on lines 1152 and 1154 also provides a reference leg formed of shielded GMR element GA and resistor RB. The selected cell and the reference leg complete a wheatstone bridge circuit across which amplifier A20 inputs are connected. Amplifier A20 responds in a manner similar to amplifier A10 discussed above to provide sensor conductivity signal SG on line 1117 to terminal T1.

Signal SG conveys indicia of conductivity of all GMR sensors in the array in according to a time division multiplex scheme. When an array sensor 1100 is used for each sensor in sensor group 810, process controller 214 additionally receives signal SYNC on line 837. Signal SYNC is provided by NAND gate 1190 on line 1192 to terminal T7 once for every complete scan of array 1115, that is when one particular cell is selected (e.g., cell 1120 at $X_0$, $Y_0$).

Each GMR element of array 1115 provides an independent sensitivity region for PMP detection. By facilitating a large number of sensitivity regions into one specimen, measurements of PMP concentration may be made with greater resolution. To compensate for variations in sensitivity between cells in array 1115, the amplitude of the drive signal(s) to internal coil K1 (or coils) or to external coil K2 may be varied in a sequence of amplitudes, for example, in synchronism with a clock signal on terminal T6 and signal SYNC on terminal T7.

Figure 12:
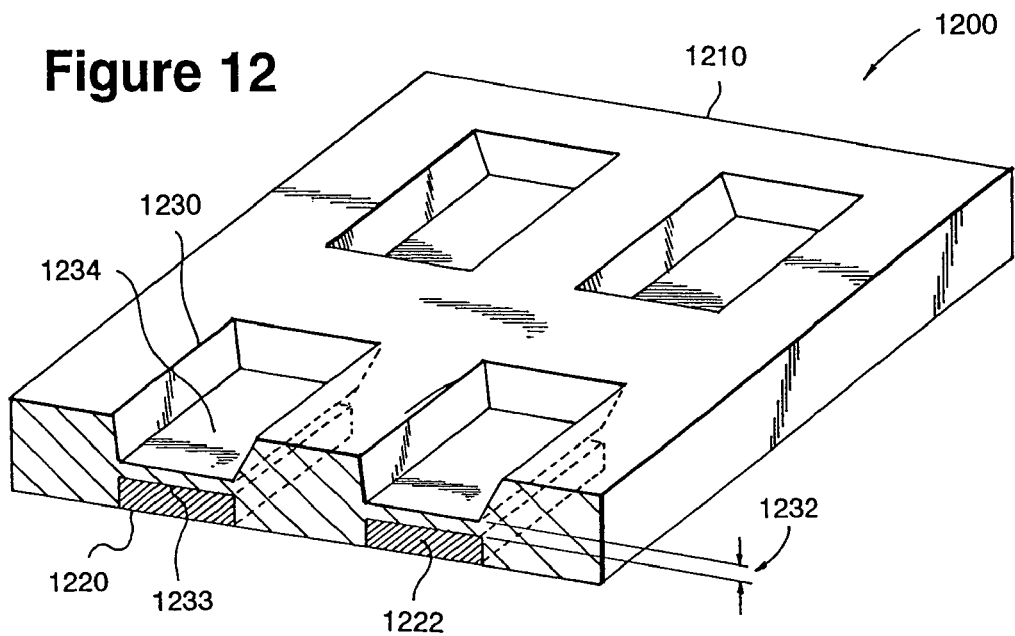
FIG. 12 is a perspective view of a portion of a specimen carrier in a variation according to the present invention.

A specimen carrier according to various aspects of the present invention includes any fluid container that facilitates mounting a sensor a fixed distance from a surface internal to the container. For example, specimen carrier 1200 in partial cross section in FIG. 12 includes a block of material 1210 having an array of containers 1230 formed therein. Each container 1230 includes a surface 1234 for contact with a fluid specimen. Surface 1234 is of the type on which PMPs are bound as discussed above. A sensor integrated circuit 1220 is mounted a fixed predetermined distance 1232 below each respective surface 1234 of each container in the array. Sensor 1220 may be of the type described above with reference to FIG. 9 or of the type described above with reference to FIG. 11.

Block 1210 may be of any conventional material having dimensional stability and tolerance to frequent sterilization operations, for example, glass or plastic. Sensor 1220 may provide structural support for surface 1234 enabling distance 1232 to be less than distance 'b' of FIG. 3. Further, sensor 1220 may be sealed in place for protection. In a variation, power and measurement signaling between sensor 1220 and PMP detector 124 may be accomplished with conventional wireless techniques. In use with analyzer 114, pressurized atmosphere 340 may be eliminated because distance 1232 is fixed by fabrication of specimen carrier 1200.

Figure 13:
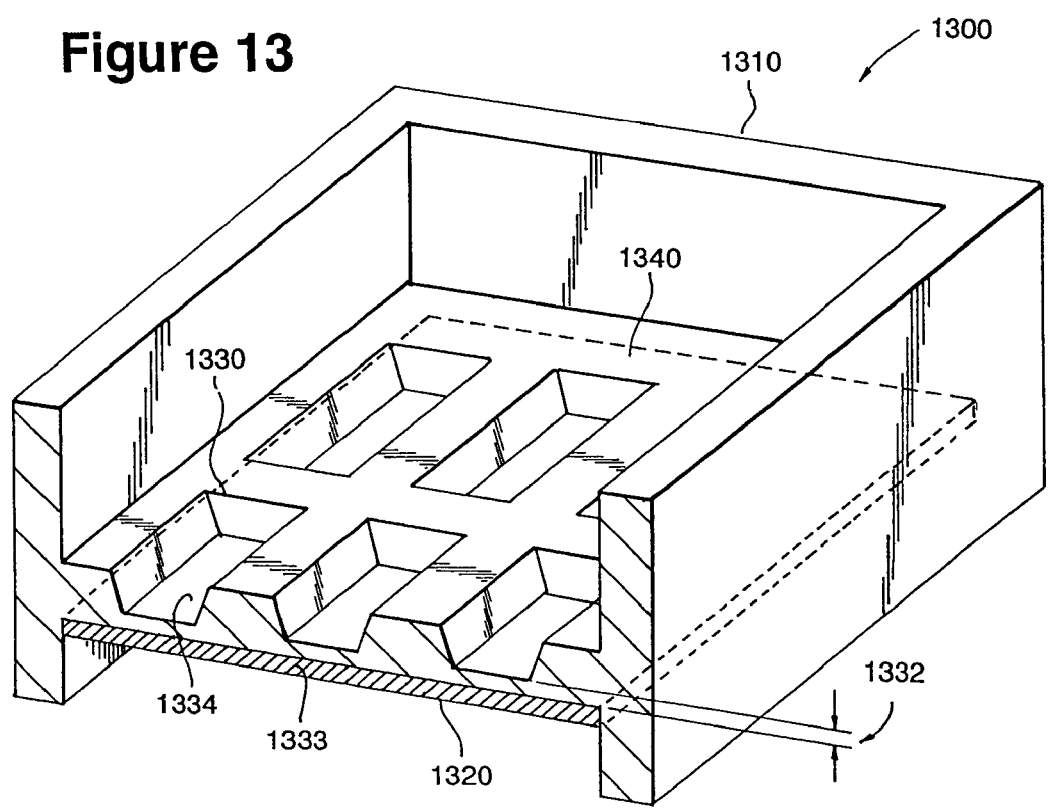
FIG. 13 is a perspective view of a portion of a receptacle in another variation according to the present invention.

An alternate specimen carrier 1300 in partial cross section in FIG. 13 includes a container wall 1310, an array 1340 of wells 1330, each having a surface 1334 to which PMPs may be bound as discussed above. Integrated circuit sensor 1320 is formed integral to specimen carrier 1300 so that distance 1332 is uniformly obtained by conventional semiconductor fabrication technology. In operation, each well 1330 is located over one GMR sensor of array 1115. Wells 1330 have dimensions so as to minimize agglomeration of multiple PMPs over a single GMR sensor so as to improve resolution of PMP concentration measurements in a single specimen contained by wall 1310.

The size of well 1330 may be small enough to mechanically permit the binding of only one PMP. In such a variation, the resolution of one molecule of a substance may be detected. In an alternate variation, the size of well 1330 may be larger than one PMP to (a) permit faster acquisition of a bound PMP to the respective surface 1334 of well 1330; or (b) permit binding of at least a minimal number of PMPs for positive detection (i.e., less chance of false positive assay results).

Each well 1330 may be coated (e.g. at step 510) for a different biochemical assay to be performed on one specimen. Multiple assays are then performed in about the same amount of time as for one assay.

In a variation, fluids discussed above, including those used for receptacle coating, PMP coating, PMP dispensing, and specimens may be in gel form or may include component reagents that form a gel before PMP detection. Gel formation is preferred when prepared recepticles or PMPs are to be stored before use or when specimen receptacles are to be stored prior to a PMP detection step. Contaminates that may contact the upper surface of a gel in a receptacle are unlikely to migrate into the sensitivity region or regions of the receptacle. In a variation tray 104 includes a cover for maintaining cleanliness and, therefore, accuracy of the biochemical assay.

What is claimed is:

1. A system for making a biochemical assay of each of a plurality of provided specimens, the system comprising:
   a. a plurality of receptacles, each receptacle for containing a respective specimen of the plurality of specimens, each receptacle comprising a surface for binding a paramagnetic particle to the surface;
   b. a detector for providing a resistance responsive to paramagnetic particle proximity to the detector in accordance with a giant magnetoresistive effect;
   c. a mechanism for positioning each respective surface in working proximity to the detector for providing a respective resistance;
   d. a controller for controlling the mechanism and for recording indicia of each respective resistance;
   wherein said detector comprises a multiplicity of physically defined active areas for independent detecting of each of a corresponding multiplicity of specimens of the plurality of specimens;
   each active area comprises a plurality of sensors, each sensor comprising an independent resistance responsive to paramagnetic particle proximity to the respective sensor in accordance with a respective giant magnetoresistive effect; and
   said controller further records indicia of resistance of each sensor.

2. The system of claim 1 wherein a motion of a respective receptacle is substantially stopped while the respective resistance is provided by the detector.

3. The system of claim 1 wherein:
   a. the detector comprises for each active area an integrated circuit comprising the plurality of sensors and a serial interface; and
   b. the controller is coupled to each serial interface for receiving indicia of resistance.

4. The system of claim 1 wherein each respective active area is aligned below a respective specimen.

5. The system of claim 4 wherein a distance between a surface and an active area is reduced by operation of an atmospheric pressure above the surface.

6. The system of claim 1 wherein the mechanism comprises:
   a. a disk for holding the plurality of specimens, the disk having a face and having an axis of rotation perpendicular to the face; and
   b. a motor for rotating the disk about the axis to position a respective specimen held by the disk in working proximity to the detector.

7. The system of claim 6 wherein each receptacle is integral to the disk.

8. The system of claim 1 wherein the mechanism comprises:
   a. a base for holding the plurality of specimens, the tray having a plurality of rows; and
   b. a motor for positioning a respective specimen held by the base in working proximity to the detector.

9. The system of claim 1 wherein the mechanism moves the detector.

10. The system of claim 1 wherein said receptacle is discarded and said sensor reused.

11. The system of claim 1 further comprising a console for operator controls, displays, and data processing, and a chemical analysis unit for performing said biochemical assay.

12. The system of claim 1 wherein said receptacles are placed in specimen trays which facilitate mechanical protection, identification, preparation, storage, handling and disposal of multiple specimen carriers.

* * * * *